United States Patent [19]

Sinclair

[11] Patent Number: 5,132,903
[45] Date of Patent: Jul. 21, 1992

[54] DIELECTRIC MEASURING APPARATUS FOR DETERMINING OIL AND WATER MIXTURES IN A WELL BOREHOLE

[75] Inventor: Paul L. Sinclair, Clear Lake Shores, Tex.

[73] Assignee: Halliburton Logging Services, Inc., Houston, Tex.

[21] Appl. No.: 540,059

[22] Filed: Jun. 19, 1990

[51] Int. Cl.$^5$ .................. G01V 1/00; G01V 3/00; E21B 49/00
[52] U.S. Cl. ......................... 364/422; 73/152; 324/318
[58] Field of Search ............... 364/422, 421; 324/324, 324/333, 338, 341, 640, 637, 639, 318, 339; 73/152

[56] References Cited

U.S. PATENT DOCUMENTS

| | | | |
|---|---|---|---|
| 3,916,685 | 11/1975 | Paap et al. | 73/152 |
| 4,009,434 | 2/1977 | McKinlay et al. | 324/341 |
| 4,514,693 | 4/1985 | Meador | 324/341 |
| 4,652,829 | 3/1987 | Safinya | 324/341 |
| 4,689,572 | 8/1987 | Clark | 324/341 |
| 4,812,739 | 3/1989 | Swanson | 324/640 |
| 4,820,970 | 4/1989 | Swanson | 324/640 |
| 4,839,594 | 6/1989 | Misic et al. | 324/318 |
| 4,912,971 | 4/1990 | Jeambey | 324/639 |

Primary Examiner—Dale M. Shaw
Assistant Examiner—Xuong M. Chung
Attorney, Agent, or Firm—William J. Beard

[57] ABSTRACT

A method and apparatus for measuring a mixture of oil and water in a well borehole is set forth. The measurement is a measurement of mixture dielectric constant obtained by exposing a pair of windows to the mixture of well borehole liquids. Each window is formed in coaxial cable portions having cuts in the respective surrounding ground sheaths thereof wherein the sheaths are positioned so that the windows are adjacent and parallel. The two windows form a gap which may be approximately three times wider than the windows formed in the sheath. A signal generator drives the system at a specified voltage and frequency, and changes in signal coupled between the cables are measured where the changes derive from changes in the dielectric constant of the mixture of oil and water coupled in the circuit.

16 Claims, 3 Drawing Sheets

DIELECTRIC MEASURING APPARATUS FOR DETERMINING OIL AND WATER MIXTURES IN A WELL BOREHOLE

BACKGROUND OF THE DISCLOSURE

This disclosure is directed to systems for measuring the dielectric constant of well bore fluids which provide an output indicative of the dielectric constant, and hence an indication of oil and water mixture in a well borehole. In drilling a well, formation fluids which are a mixture of oil and water are often produced. After the well has been drilled and during production, it may again produce a mixture of oil and water. This mixture may change over a period of time so that measurement of the ratio of oil and water is important to proper production of the well. In summary, an important characteristic is the ratio or mixture of oil and water. The present apparatus takes advantage of the differences in dielectric constant of the mixture of the two constituents in the well borehole fluids. Water has a dielectric constant about twenty times greater than that of oil.

The present apparatus utilizes quite high frequencies which are coupled through coaxial lines with appropriately connected terminations to thereby couple electrically the fluid into the line for obtaining transmission measurements. Substantially, the response is independent of temperature and is a response from a relatively large volume of fluid to avoid localized irregularities. It utilizes conductors of coaxial construction extending from a sonde into the fluid in one embodiment, or submerged in fluid within the sonde so that the mixture of produced oil and water from the well can be measured. It utilizes a coaxial cable, and in particular two lengths thereof, the two lengths of cable being mechanically coupled by means of an appropriately constructed window further having a coupling relationship through the window. In other words, the transmitted signal is coupled through the window into the liquid which submerges the immediate vicinity of the sonde. The output can be read at a particular terminal in the form of an output voltage. The output voltage can be converted by means of relatively linear calibrations so that the output is a correctly indicated measure of percent of oil and water in the well bore fluids. To this end, the equipment preferably utilizes a microwave generator which serves as a transmitter and appropriate lengths of coaxial cable terminating at an appropriate matched load or resistance together with a signal detection circuit.

The present apparatus can be used in a continuous wave (CW) mode so that it is able to provide a continual reading as the supportive sonde is moved along the well borehole. The output can be calibrated relative to known mixtures so that output voltages relative to the mixtures can be calibrated to read either in volts or directly in percent mixture of water and oil.

BRIEF SUMMARY OF THE PRESENT APPARATUS

This apparatus is summarized as a coaxial cable system connected as an antenna and includes a high frequency signal generator, a segment of cable, a mixer, and another segment of cable which terminates at a suitable and preferably matched resistive load. This reduces the standing waves on the cable system. The two sections of cable may be joined together and a window cut in the shield of each cable. The window has a specified length, and is further defined by gaps of a specified width in the shields around the two sections of cable. This permits the surrounding fluid to move into close proximity to the window and thereby form a capacitive coupling medium which is related to the dielectric properties of the medium, and that in turn is dependent on the effective bulk dielectric constant of the oil and water mixture.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
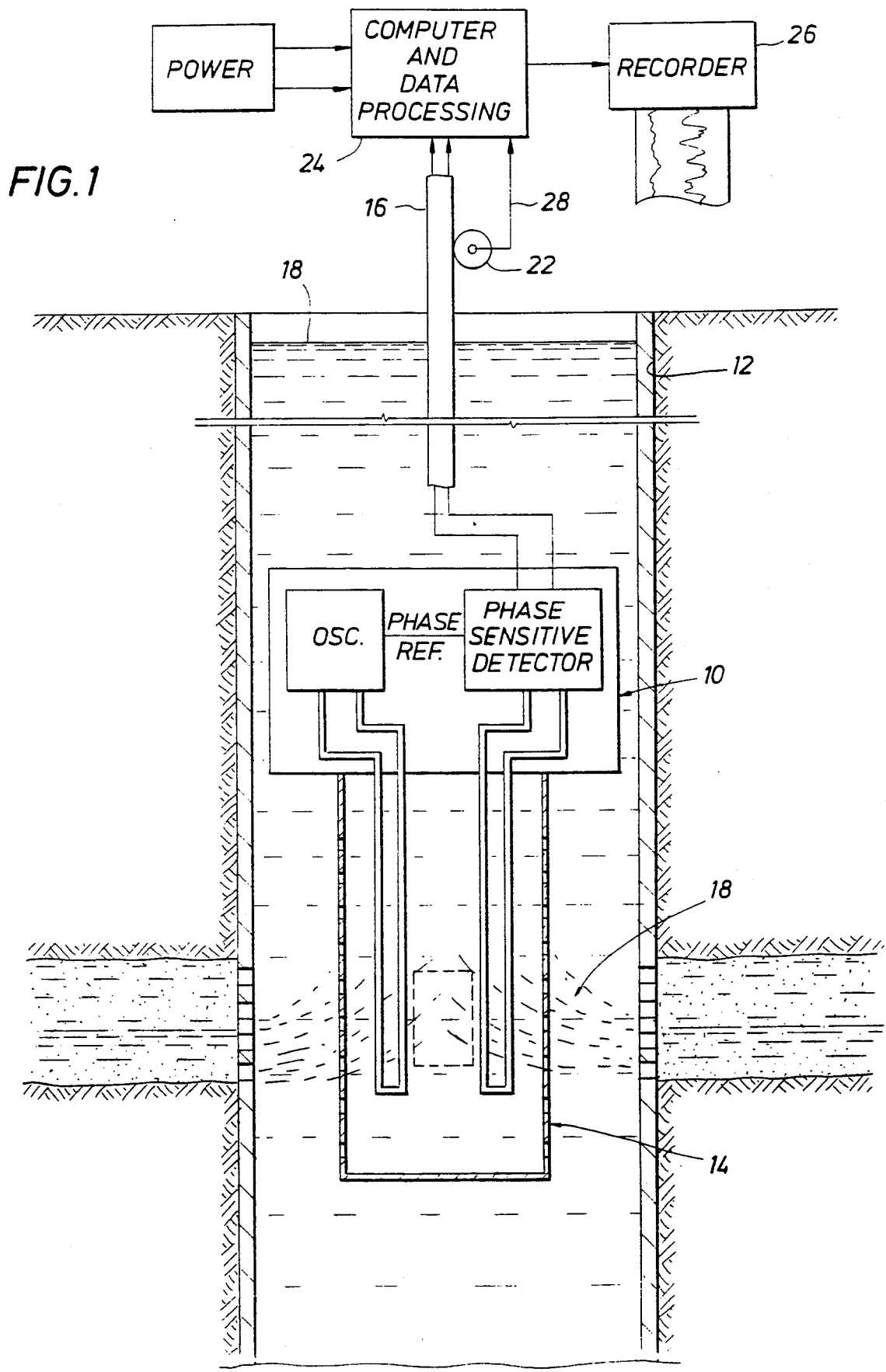
FIG. 1 shows a sonde supported on a logging cable in a well borehole in an oil and water mixture for measuring the dielectric thereof to determine the relative concentration of water and oil and the mixture.

Attention is now directed to FIG. 1 of the drawings which shows the dielectric measuring apparatus 10 of the present disclosure positioned in a well borehole 12, typically uncased, but equally useful for a cased well, wherein the apparatus is placed within a sonde 14 suspended on a logging cable 16 and completely submerged in oil, water or a mixture thereof identified at 18. The logging cable 16 extends to the surface and passes over a sheave and is spooled on a large supply reel or drum 22. There are one or more electrical conductors in the armored logging cable which connect from the sonde 14 to a CPU 24 which operates to execute and carry out the various and sundry activities which are required of the equipment. Control signals are sent down the logging cable and data is received up the logging cable. The output is provided from the CPU 24 to a recorder 26. The data of interest is recorded, and typically it is helpful to furnish this data as a function of depth. Depth is indicated by an electrical or mechanical depth measuring apparatus 28 which typically measures cable length dependent on travel of the cable 16 over the sheave. Typically, the sonde 14 is lowered into the well and is submerged at a selected depth. The depth is noted. Measurements of the liquid accumulating in the well are taken and are provided for surface inspection. A typical output from the present apparatus indicates that the liquid accumulated in the well is a specific percentage of oil and water in ratios ranging from pure oil to pure water and percentages in between.

The present apparatus is relatively small in the sense that the antenna which is exposed to the liquid 18 is quite small. It has been shown in FIG. 1 to be enclosed in a sonde chamber perforated to allow free passage of borehole fluids, or external of the sonde 14. The apparatus can be on the exterior, but for protection against banging during transit along the well borehole, the antenna is placed within a chamber in the sonde which is exposed to well fluids. In any event, the dielectric sensing mechanism is arranged so that an antenna system is included at a location which is exposed to the mixture of oil and water in the well borehole.

Figure 2:
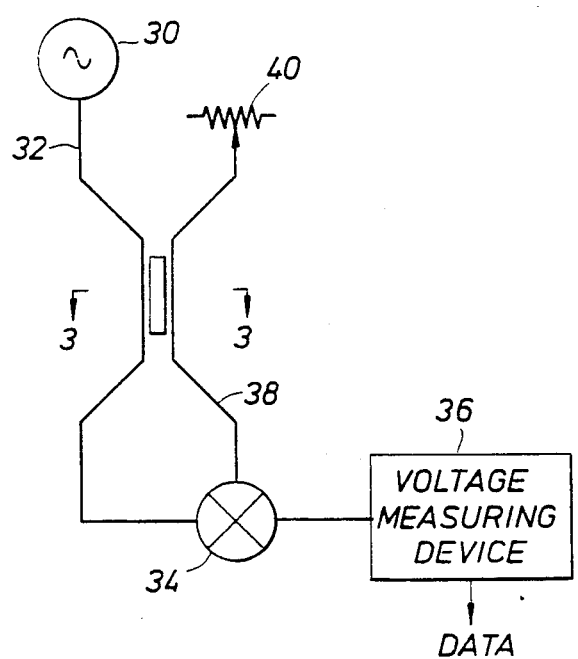
FIG. 2 shows a schematic of the generator and coaxial cable system arranged for operation of the present sensor system.

Going now to FIG. 2 of the drawings, equipment located in the sonde includes an adjustable frequency AC signal generator 30 which forms an output on a coaxial cable 32. The cable 32 connects to a mixer 34 which has an additional output to a voltage measuring device 36. In addition, another port of the mixer 34 connects with a second coaxial cable 38 and that extends to the cable load 40. The coaxial cables 32 and 38 are joined together and form an antenna system which integrates the well borehole fluids as part of the dielectric as will be described. The operation of the system shown in FIG. 2 is better understood when scale values are placed thereon.

Figure 3:
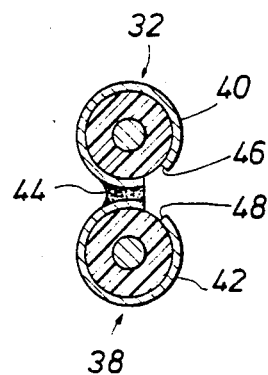
FIG. 3 of the drawings is a sectional view along the line 3—3 of FIG. 2 showing signal interconnection of the two coaxial cables with windows cut therein and a defined gap for interjecting surrounding fluid into the system for measurement.

As a generalization, the generator 30 is a frequency adjustable oscillator which forms an output signal at a fixed voltage. A low level or signal voltage is all that is needed. The generator 30 preferably forms an output signal in the megahertz range. The frequency can be quite high, even up into the range of a few gigahertz. In a representative system, the generator can operate at 2.5 GHz. For operation at this frequency level, the output is provided to the coaxial cable 32 which has a characteristic impedance. To this end, the termination 40 matches the characteristic impedance so that a standing wave is not formed on reflection from the termination 40. Consider a typical coaxial cable. Utilizing cable having a Teflon dielectric wherein the cable may be described as semi-rigid and the cable segments 32 and 38 are each about one meter in length, they have common diameters of about 0.141 inches, and the cables 32 and 38 are joined in the fashion shown in FIG. 3. The cables are identical, typically being obtained from the same supply spool. Both of the cables have a central conductor which is one or multiple strands which is surrounded by a dielectric sleeve of cylindrical construction. The outer sheath of the cable is typically an extruded solid copper tubular shield which is formed into a ground screen or shield. The outer sheath may also be made of a corrosion-resistant alloy plated with copper on the inside surface to provide high electrical conductivity. Here, the cable 32 has the sheath 40 while the cable 38 has the sheath 42. The two sheaths are soldered together at 44 where a fillet of solder is placed between them. The fillet has a length which will be described and has a width which is sufficient to bind the two cables together and is provided only for mechanical stability. Both sheaths 40 and 42 have small lengthwise parallel windows cut therein, the windows being identified at 46 and 48. The two windows cooperate to define a dielectric gap between the two cables which is filled with the liquid in the well borehole, and liquid in that particular gap is measured. In other words, the windows formed in the two cables introduce the dielectric of the liquid into the system.

The cuts which are formed define a lengthwise window. The length of the windows is related to the frequency of the signal generator, and has an upper limit which is determined by the frequency and signal propagation velocity along the cable. Thus, the cable window L is given by $c/[2f(K)^{\frac{1}{2}}]$. The symbol c is the velocity of light while f is the frequency of the oscillator 30. K is the dielectric constant of the cable insulator. This defines a maximum or upper limit for the window length. If Teflon is the dielectric and the generator frequency is 2.5 gigahertz, the window length is typically about 4 centimeters. The windows 46 and 48 have a limited width which is generally determined by the need to minimize variations in the cable characteristic impedance that enable proper or acceptable internal reflections versus increases in signal coupling when the window is wider. An acceptable compromise between these two contradictory factors is a width which is about one tenth the internal circumference of the insulator sleeve within the cable.

When the cables 32 and 38 are joined in the fashion shown, coupling between the two cables occurs by electric field and magnetic field interaction between the two cables. The measure of coupling through the respective windows is in part determined by the impedance of the gap between the two windows. That gap in turn is dependent on the physical dimensions of the gap and also on the dielectric constant of the materials in the gap. As a generalization, coupling through the respective windows from one cable to the other may be by electric field coupling in which event the coupled system incorporating the surrounding well borehole fluids is especially sensitive to the dielectric constant of the materials that are in the gap. The gap is defined as the cable to cable measure across the full width of the two windows considered jointly. The windows, however, refer to the width of the cuts in the outer sheath or shield of the cables. An acceptable ratio is a window to gap width ratio of about 1:3. The coupling through the two windows incorporates the gap as mentioned and the material that is in that gap so that the liquid becomes a part of the circuit. The equivalent circuit involved in this two window and gap arrangement involves a relationship where the output voltage is given by a relationship generally being $V = G\ V_o f Z_o$. In the foregoing, G incorporates coupling capacitance and other geometrical variables that are fixed for a particular sized assembly, and $V_o$ is the generator output voltage, $Z_o$ is the cable characteristic impedance, and f is the frequency of the generator. It will be observed that the output voltage is generally a linear function of frequency; as frequency increases, the output voltage increases. The constant G may be computed from the dimensions of the apparatus, but is preferably determined by calibration to compensate for typical small manufacturing variations.

Figure 4:
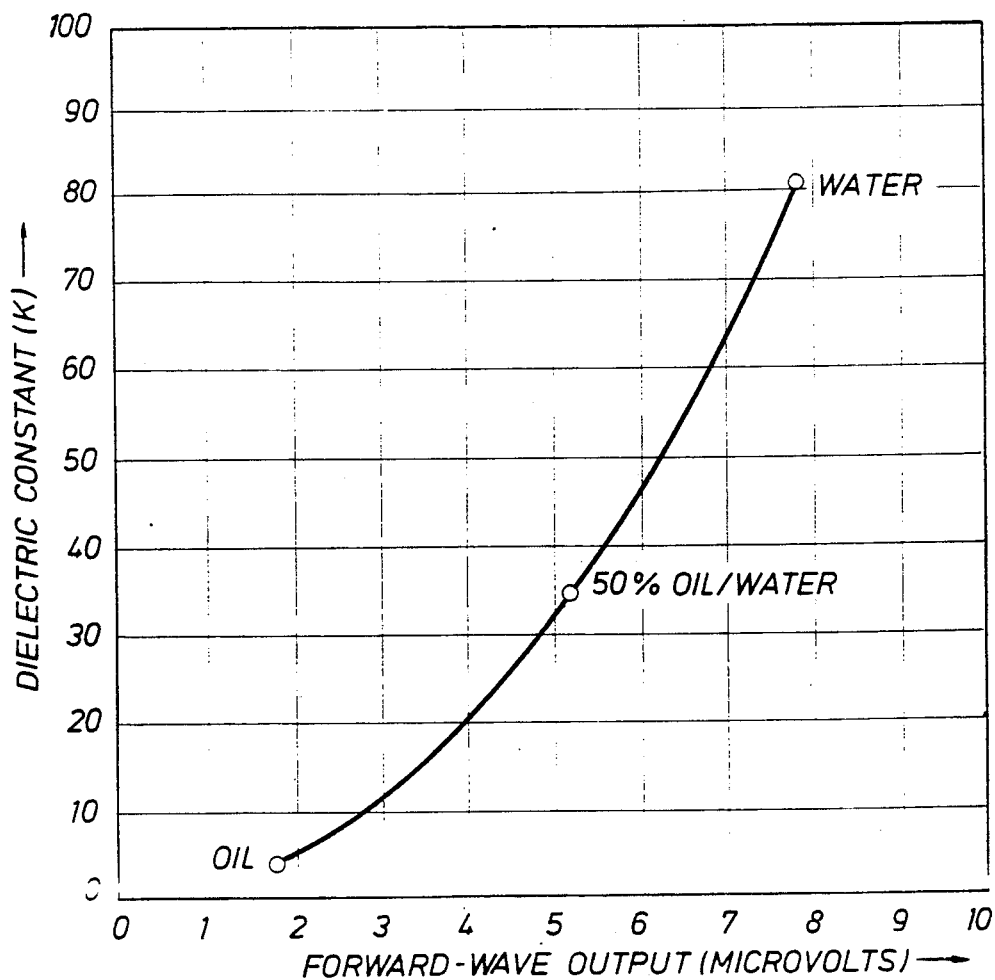
FIG. 4 is a plot of dielectric constant versus output voltage to show variations in oil and water mixture encoded by a change in voltage.

Utilizing the foregoing arrangement, and operating at frequencies even as high as 5 GHz, output voltages have been observed that are sufficiently sized to be measurable. By contrast, lower frequencies can be used, even in the range of 200 MHz with a reduction in measurement accuracy. Consider a particular example which is set out in FIG. 4. There, the dielectric can be as much as about 81 which is the dielectric constant of pure water. Oil has a much lower dielectric constant of about 4 so that the 100 percent oil data point is also shown.

The midpoint further shows a fifty percent mixture of oil and water. The output voltage (measured in microvolts) is proportionate to dielectric constant and thus provides the desired measured result. The operating frequency which can be as high as 5 GHz; the data of FIG. 4 was obtained at 2.5 GHz. It is generally preferable to operate at higher frequencies because they are less sensitive to salt dependent changes where substantial quantities of salt are dissolved in the water. Of course, there are other impurities which may be carried in the liquid and they may have a different kind of impact on the measured data.

The present apparatus can be used to obtain an indication of percent of oil and water mixture which is non-linearly proportionate to output voltage. The voltage is simply measured and the output data provides the appropriate indication according to calibration of the sort shown in FIG. 4 for a particular frequency of operation. By use of calibration charts such as this, changes in scale values such as operating frequency, changes in cable window and gap size, changes in cable characteristic impedance, and the like can be accommodated quite easily. Moreover, the system is relatively simple in that it has no moving parts and provides a substantially instantaneous reading which quickly reflects changes in the percent mixture.

Figure 5:
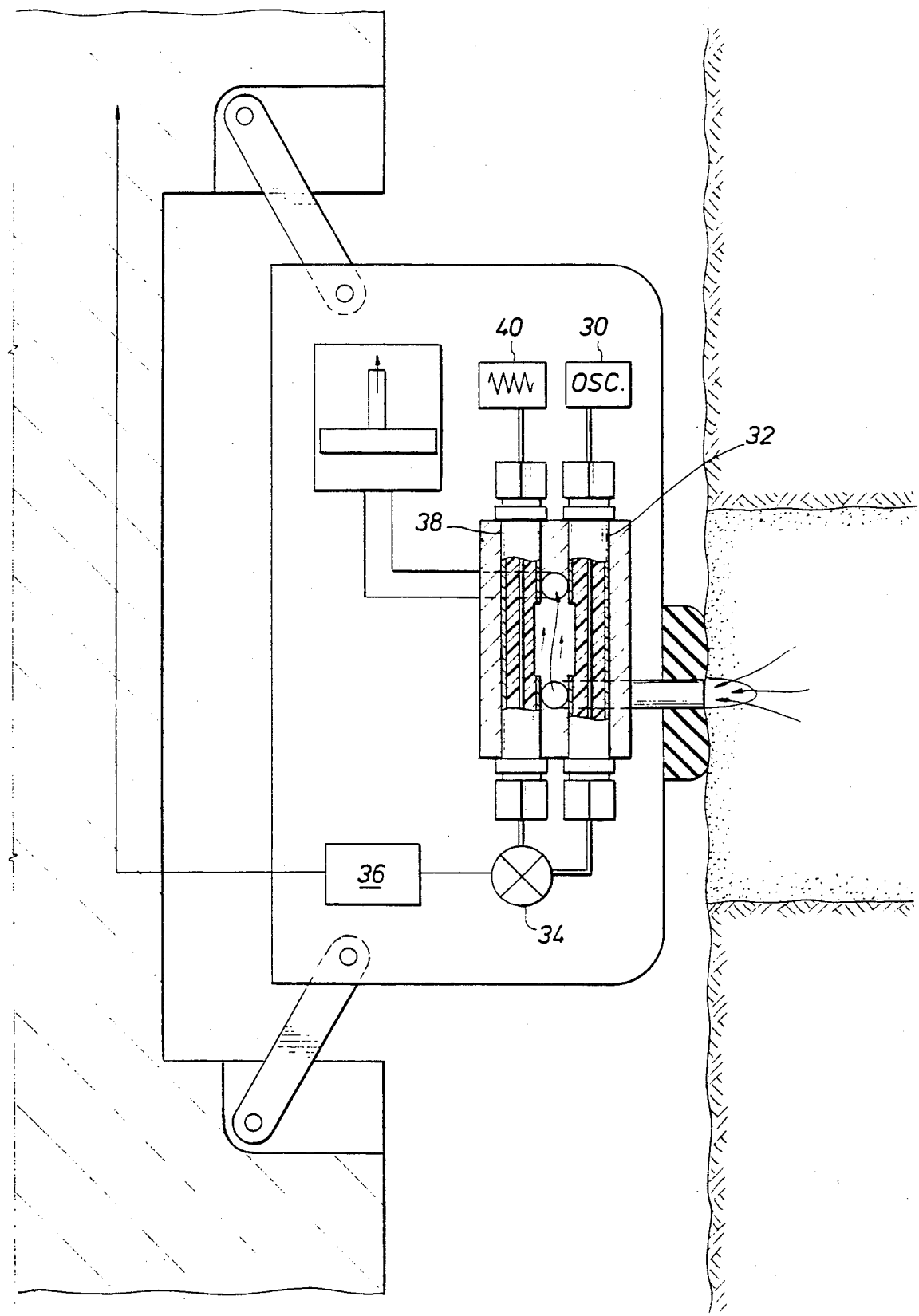
FIG. 5 is a drawing of an enclosed version of the invention in conjunction with a formation testing apparatus to sample formation fluids.

The cable gap can be flush mounted on the sonde also. Physical bending of the coaxial cables is permitted so long as the windows preferably lie in a common plane arrangement parallel to one another and are generally straight. Moreover, the sensitive region which is the window is best exposed to large volumes of fluid; spot irregularities are thus reduced, or even eliminated. Furthermore, the exposure of the cable with the windows permits rapid readings to be obtained as the sonde moves along the well borehole at great speed or at no speed. That is, the sonde can be stationary if desired. In this regard, the present invention may also be installed in formation tester logging tools as shown in FIG. 5. During exploratory logging of freshly-drilled boreholes, it is often desirable to draw samples of connate fluid from a rock formation of interest intersected by the borehole. In a known fashion, a pad is forced against the borehole wall to provide a fluid-tight seal, and a mechanical pump draws a sample of fluid to enable the fluid properties (e.g., pressure) to be measured. In FIG. 5, the fluid is pumped between coupled transmission lines as indicated by the arrows depicting fluid flow within the body of the testing tool while the dielectric properties are measured as described with respect to FIGS. 2 and 3. Component numerals and functions in FIG. 5 correspond to FIG. 2. This method provides a novel means to directly determine the oil/water concentrations of selected intervals of rock formations.

While the foregoing is directed to the preferred embodiment, the scope thereof is determined by the claims which follow.

What is claimed is:

1. An apparatus for measuring a relative mixture of oil and water in a well borehole, comprising:
    (a) a high frequency signal generator for forming an output signal at a specified frequency;
    (b) a coaxial cable means having a central conductor surrounded by an external shield therearound and separated by a central insulator wherein the conductor is connected to said signal generator for providing a high frequency signal flow path;
    (c) a window formed in said cable means wherein the window is exposed to oil and water and mixtures thereof in the well borehole to thereby form a circuit load on the cable means in part dependent on the mixture of liquids in the well borehole; and
    (d) measuring means connected to said cable for providing an indication of circuit variations on said cable means as a result of mixture variations in liquid in the well borehole wherein the output of said measuring means reflects variations in percentage of oil and water in the mixture.

2. The apparatus of claim 1 wherein said coaxial cable means comprises a first and a second segment, the first segment being positioned parallel to the second segment wherein a plurality of parallel and adjacent windows are cut in both of said segments external shields, and further wherein said windows define a gap of exposure to the liquids in the well borehole.

3. The apparatus of claim 2 wherein said first and second segments connect with a signal mixer at one cable end and said first and second segments connect to a voltage measuring means.

4. The apparatus of claim 2 wherein said first and second segments connects with a phase sensitive detector at one cable end and said first and second segments connect to a voltage measuring means.

5. The apparatus of claim 2 wherein said first and second segments have a common characteristics impedance, and said first and second segments are serially connected to said measuring means, and said first and second segments terminate at a load matching the characteristic impedance of said first and second segments.

6. The apparatus of claim 2 wherein said windows form a gap having a length related to the frequency of the signal generator, and wherein said gap has a width less than the length thereof.

7. The apparatus of claim 2 wherein the shields of said first and second segments are soldered together.

8. The apparatus of claim 2 wherein windows are provided in the shields of said first and second segments said windows having a width approximately equal to about one third of the cable diameter.

9. The apparatus of claim 8 wherein said windows have a common width and that width is approximately one third of the width of the gap.

10. The apparatus of claim 9 wherein said windows have equal length.

11. The apparatus of claim 9 wherein said windows face one another and permit well borehole liquids into the gap therebetween.

12. A method of measuring a relative liquid mixture of oil and water in a well borehole, comprising the steps of:
    (a) lowering down a well borehole into the accumulated liquid therein an exposed pair of insulated, shield equipped conduit conductor portions, wherein said portions have windows formed in the respective shields thereof to define a gap therebetween;
    (b) exposing the gap to the liquid mixture in the well borehole;
    (c) placing a selected voltage signal at a specified frequency on said shield equipped conduit;
    (d) measuring the impedance of said shield equipped conduit influenced by the liquid mixture wherein the measurements represent the changes in relative percentage of oil and water in the liquid in the well borehole; and (e) measuring the changes in signal voltage coupled from one shield equipped conduit portion to the other shield equipped conduit portion wherein the measurement represents the changes in relative percent of the oil and water in the liquid in the well borehole.

13. The method of claim 12 including the step of driving one of the pair of shield equipped conduits with the selected signal, connecting both of said shield equipped conduit to a mixer for mixing, and connecting one end of the pair of shield equipped conduits to a matching load.

14. The method of claim 13 including the step of measuring an output voltage signal from said mixer.

15. The method of claim 14 including the step of calibrating said measured voltage against oil/water mixture percentage.

16. The method of claim 15 including sid measured voltage against the mixture percentage from 100% oil to 100% water.

* * * * *